United States Patent [19]
Bombardelli et al.

[11] Patent Number: 5,118,671
[45] Date of Patent: Jun. 2, 1992

[54] COMPLEXES OF AESCIN, β-SITOSTEROL OR CHOLESTEROL, AND PHOSPHOLIPIDS AND PHARMACEUTICAL COMPOSITIONS CONTAINING THEM

[75] Inventors: Ezio Bombardelli; Gianfranco Patri; Roberto Pozzi, all of Milan, Italy

[73] Assignee: Indena S.p.A., Milan, Italy

[21] Appl. No.: 629,843

[22] Filed: Dec. 19, 1990

Related U.S. Application Data

[63] Continuation-in-part of Ser. No. 514,126, Apr. 25, 1990, abandoned, which is a continuation of Ser. No. 158,577, Feb. 22, 1988, abandoned.

[30] Foreign Application Priority Data

Feb. 26, 1987 [IT] Italy .............................. 19496 A/87

[51] Int. Cl.$^5$ ................ A61K 31/705; A61K 31/575; A61K 31/685
[52] U.S. Cl. ........................ 514/26; 514/33; 514/182; 536/4.1; 536/5; 536/117
[58] Field of Search ............ 514/26, 33, 182; 536/4.1, 5, 17.1, 18.1, 55.3, 117; 260/403

[56] References Cited

U.S. PATENT DOCUMENTS

| | | | |
|---|---|---|---|
| 4,101,652 | 7/1978 | Bonati | 536/4.1 |
| 4,624,919 | 11/1986 | Kokusho et al. | 536/17.1 |

FOREIGN PATENT DOCUMENTS

| | | |
|---|---|---|
| 0462710 | 1/1950 | Canada . |
| 0142193 | 5/1985 | European Pat. Off. . |
| 0283713 | 9/1988 | European Pat. Off. . |
| 1217547 | 5/1966 | Fed. Rep. of Germany . |
| 62-238299 | 10/1987 | Japan . |

OTHER PUBLICATIONS

Assa et al; Biochim. Biophys. Acta 307:83–91 (1973).
Elias et al; J. Histochem. Cytochem. 27(9):1247–1260 (1979).
Nakamura et al; Chem. Pharm. Bull. 29(6):1681–1688 (1981).
Yu et al; Chem.-Biol. Interactions 52:185–202 (1984).

*Primary Examiner*—Ronald W. Griffin
*Assistant Examiner*—Nancy S. Carson
*Attorney, Agent, or Firm*—Bucknam and Archer

[57] ABSTRACT

Complexes formed between aescin, cholesterol or β-sitosterol and phospholipids are described. The molar ratio of phospholipids to aescin/β-sitosterol or cholesterol is from 0.5 to 2. The phospholipids are selected from the group of soy or egg lecithins, phospholipids from bovine or swine brain or cutis, phosphatidylcholine, phospatidylserine, phosphatidylethanolamine in which the acyl groups may be the same or different and are mostly derived from palmitic, stearic, oleic, linoleic, linolenic acids, for instance, pharmaceutical compositions and a method for producing an anti-inflammatory effect in an animal are also described.

6 Claims, No Drawings

COMPLEXES OF AESCIN, β-SITOSTEROL OR CHOLESTEROL, AND PHOSPHOLIPIDS AND PHARMACEUTICAL COMPOSITIONS CONTAINING THEM

This application is a continuation-in-part of U.S. Ser. No. 514,215 filed Apr. 25, 1990, now abandoned, which is a continuation of Ser. No. 07/158,577, filed Feb. 22, 1988, now abandoned.

The present invention relates to complexes formed between aescin, cholesterol or β-sitosterol, and phospholipids, and to pharmaceutical and/or cosmetic compositions containing them.

Aescin is a saponin obtained from *Aesculus hippocastanum* seeds and it is already used in pharmaceutical field as anti-edematous or vasotonic agent.

Its use has been however restricted by several drawbacks, particularly:

1) poor absorption by oral route, partly due to fast bacterial degradation in the gastro-enteric tract, or to a complexation with cholesterol or biliary acids;

2) poor tolerability by cutaneous/topical administration, involving irritative phenomena of some seriousness.

In order to overcome some of these drawbacks, aescin has been complexed with β-sitosterol or with cholesterol (U.S. Pat. No. 4,101,652). Saponin/phospholipid complexes are known from DE 1217547. Now it has surprisingly been found that complexes with phospholipids of aescin complexed with β-sitosterol or with cholesterol allow an effective absorption by topical and oral route due to the lipophilic characteristics attained.

Pharmacological activity and tolerability also turned out to be surprisingly enhanced.

The use of the complexes of the invention proved to be particularly convenient because the double complexation effectively reduced the hemolytic index and the irritating action on cutis and mucose of aescin.

The phospholipids that can be used according to this invention may be either vegetal or synthetic in nature, with acyl residues being the same or different, ad shown by the formula:

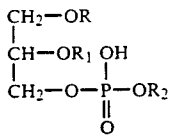

wherein R and $R_1$, which are the same of different, are mostly acyl residues of the palmitic, stearic, oleic, linoleic, linolenic acids, while $R_2$ is the residue of choline, ethanolamine or serine. Particularly preferred phospholipids for use in cosmetics are the vegetal or naturally occurring phospholipids, such as those obtained from soy or from bovine or swine cutis or brain, similar to the ones that are found in human dermis; for other uses, a phospholipid which is chemically homogeneous and defined in its structure units (acyl and phosphoryl-amine groups) is preferred.

The complexes according to the invention are prepared by reacting the aescin/β-sitosterol or cholesterol complex with the phospholipids in an aprotic solvent.

The molar ratios of the phospholipids to aescin/β-sitosterol or cholesterol complex are in the range from 0,5 to 2, more preferable about 1.

After solubilization has been completed, the complex compounds are isolated by removing the solvent under vacuum, by freeze drying or by precipitation with non-solvents.

The thus obtained complexes are lipophilic in character and soluble in apolar and aprotic solvents, in which the individual components of the complex are normally insoluble.

The formation of a molecular complex is confirmed by a NMR spectroscopy study of the proton, carbon-13 and phosphorus, by comparing the spectra of the individual constituents with those of the reaction product. In the H-NMR spectrum of the complexes, the signals from the protons of the lipid chain are well evident, as well as a broadening of the band of $N-(Me)_3$ group of choline, showing that this moiety is involved in the complex compound.

In the $^{13}C$-NMR spectrum, the value of the relaxation times of the nuclei that are most involved in the complex's formation is reduced in a similar manner to the proton spectrum, until disappearance of all the signals characteristic of the terpene moiety of the saponin takes place. In the $^{31}P$-NMR spectrum, a substantial broadening of the phosphorus band is observed with an evident peak shift. From these data, it can be deduced that, in the formation of the complex compound, the saponin is bound to the phospholipid by engagement with the polar head of this latter; the lipophilic character is imparted upon the complex compound by the lipid chains, which can freely rotate in the medium, as it can be deduced from their H-NMR spectrum, which shows no changes.

The complexes prepared according to the invention were tested pharmacologically: the complexed forms prove to be more active than the corresponding free or partially complexed forms.

Table 1 shows the results obtained in the Croton oil test: it is clear that the aescin/β-sitosterol/distearoyl-phosphatidylcholine complex is significantly more active not only than the free components but also than the aescin/distearoyl phosphatidylcholine complex or the aescin/sterol complex.

From the applicative point of view, the complex obtained as above, can be employed as microdispersions in water by preparing them by homogenization using high-speed stirrers or ultrasonic procedures, or they may be incorporated as such into appropriate pharmaceutical or cosmetic preparations.

For topical administration, it is convenient to use the above mentioned microdispersion, which may be optionally added with thickening agents, said microdispersions can contain very wide percentages of active ingredient, from 0,1 to 30%, and may also be incorporated in forms of gels or emulsions for dermatologic or cosmetic purposes, or used as such as above mentioned. The complexes, due to their high lipophilia, may be dissolved in oils, in which they are stable, or incorporated in water/oil emulsions, or may be used in the preparation of capsules, tablets or suppositories.

In the preparation of the pharmaceutical compositions, care must be taken in using solvents, some of which, for examples alcohols and those having a high dielectric constant, such as dimethylsulfoxide, cleave the complexes, as evidenced by NMR spectroscopy. In fact, complexes dissolved in said solvents show spectra which substantially correspond to the summatory of spectra separately registered for the single constituents.

Therefore, in the formulations the compatibility of the compound with the dispersing medium must be taken into account, in order to safeguard complex stability and consequently activity.

Advantageously, in view of the higher activity of the complexed forms according to the invention, the dosage of the active ingredient may, under certain circumstances, be reduced, the specific activity remaining unchanged.

Suitable forms for pharmaceutical and/or cosmetic uses by topical application, are creams, gels or aqueous microdispersions containing 0,1 to 30% by weight of aescin/$\beta$-sitosterol or cholesterol/phospholipid complex. These forms will be administered one or several times daily, depending on the intended use. Suitable forms for pharmaceutical uses, by oral administration, are tablets, capsules, syrups, granules, solutions, which contain unit doses of the complexed active principle in the range from 1 to 500 mg. These pharmaceutical forms will be administered once or several times a day, depending on the severity of the pathology to be treated and the patient conditions.

The compositions according to the invention can in particular be used for treating conditions of inflammation, altered capillary fragility and permeability and, in general in all the fields in which an activity of the aescin is recognized at present.

EXAMPLE 1

Complex of aescin/$\beta$-sitosterol complex with soy-bean phosphatidylcholine 15,5 g of a preconstituted complex of aescin (M.W. 1140) and $\beta$-sitosterol (M.W. 412) in stoichiometric amounts (M.W. 1552) were suspended under stirring in 150 ml of ethyl-acetate and added with 15.54 g of soybean phosphatidylcholine (M.W. 777); after heating at gentle reflux of the reagents, the solution was concentrated to small volume and poured into 160 ml n-hexane. The precipitated solid material has been filtered and dried under vacuum at 30° C. until the solvent was completely removed. The 1H NMR spectrum of the final product shows protonic signals at 0,8 ppm originating from the aliphatic methyl groups of the lipidic chains, CH$_2$ signals between 1,5 and 2,8 ppm, a very broadened N—CH$_3$ signal at around 3,4 ppm, signals from hydrogens of double bonds of aliphatic chains at 5,5 ppm; signals of —CH$_3$ of $\beta$-sitosterol are present in the region between 0,8 and 1,3 ppm indicating the partial mobility of the protons of $\beta$-sitosterol.

In the carbon spectra it is remarkable the absence of the lack of resolution of the typical signals of aescin and the absence or the extreme broadening of the signals of the carbons belonging to the glycerol and choline portions of the phospholipid. This complex is freely soluble in the chlorinated solvents and in the vegetal oils.

EXAMPLE 2

Anhydrous gel containing the complex aescin/$\beta$-sitosterol/phosphatidylcholine 100 g of gel contain:

| | |
|---|---|
| acescin/$\beta$-sitosterol/phosphatidylcholine complex | 3 g |
| Tween 20 | 29 g |
| Alcohol 95% | 15 g |
| Propylene glycol | 49 g |
| Carbopol 934 | 3 g |
| Parfum | 0.9 g |
| Preservants | 0.1 g |

TABLE 1

Anti-oedema effect of tested substances at 6h (croton oil dermatitis in the mice ear. Tubaro et al., Agents Actions 17, 347, 1985)

| Substances | $\mu$M/ear | Oedema mg | Percent reduction | P (Student's test) |
|---|---|---|---|---|
| Controls | — | 7.1 ± 0.2 | — | — |
| Aescin | 0.2 $\mu$Moles | 3.7 ± 0.6 | 47.5 | <0.01 |
|  | 0.1 $\mu$Moles | 5.2 ± 0.5 | 26.8 | <0.01 |
| $\beta$-sitosterol | 0.2 $\mu$Moles | 6.2 ± 0.3 | 12.7 | <0.05 |
|  | 0.1 $\mu$Moles | 6.5 ± 0.3 | 8.5 | — |
| Distearoylphosphatidylcholine | 0.2 $\mu$Moles | 6.0 ± 0.4 | 15.5 | <0.05 |
|  | 0.1 $\mu$Moles | 6.3 ± 0.3 | 11.3 | <0.05 |
| Aescin/$\beta$-sitosterol | 0.2 $\mu$Moles | 3.7 ± 0.4 | 47.5 | <0.01 |
|  | 0.1 $\mu$Moles | 5.1 ± 0.2 | 28.2 | <0.01 |
| Aescin/distearoylphosphatidylcholine | 0.2 $\mu$Moles | 4.2 ± 0.5 | 40.8 | <0.01 |
|  | 0.1 $\mu$Moles | 5.5 ± 0.4 | 22.5 | <0.01 |
| Aescin/$\beta$-sitosterol/distearoylphosphatidylcholine | 0.1 $\mu$Moles | 0.6 ± 0.2 | 83.6 | <0.001 |
|  | 0.05 $\mu$Moles | 3.6 ± 0.5 | 45.9 | <0.005 |
| Indomethacin | 0.6 $\mu$Moles | 3.4 ± 0.4 | 58.1 | <0.001 |

We claim:

1. A complex formed from 1) preconstituted aescin-cholesterol or aescin-$\beta$-sitosterol complex and 2) a phospholipid wherein said preconstituted complex of aescin-cholesterol or aescin-$\beta$-sitosterol is formed by reacting aescin and cholesterol or $\beta$-sitosterol in stoichiometric amounts and, where the molar ratio of said phospholipid to said aescin/cholesterol or aescin/$\beta$-sitosterol complex is between 0.5 to 2.

2. The complex according to claim 1 wherein said ratio is about 1.

3. The complex according to claim 2 wherein said phospholipid is a member selected from the group consisting of soy or egg lecithins, phospholipids from bovine or swine brain or cutis, phosphatidylcholine, phosphatidylserine, and phosphatidylethanolamine, said phospholipid having acyl groups which are the same or different and which are derived from an acid selected from the group consisting of palmitic, stearic, oleic, linoleic, and linolenic acids.

4. The complex according to claim 3 wherein the phospholipid is distearoylphosphatidylcholine.

5. A pharmaceutical composition comprising as active ingredient 0.1-30% by weight of a complex formed from preconstituted 1) aescin-cholesterol or aescin-$\beta$-sitosterol and 2) a phospholipid and a pharmaceutically acceptable diluent or carrier.

6. A method of producing an anti-inflammatory effect in a living subject which consists of administering to said living subject in need of treatment an anti-inflammatory effective amount of a composition containing 1-500 mgs of a complex formed from component 1) which is preconstituted aescin-cholesterol or aescin-$\beta$-sitosterol and component 2) which is a phospholipid, said component 1) and 2) having been reacted in the molar ratio of 1.

* * * * *